United States Patent [19]

Agreda et al.

[11] Patent Number: 4,939,294

[45] Date of Patent: Jul. 3, 1990

[54] PREPARATION OF ULTRA HIGH PURITY METHYL ACETATE

[75] Inventors: Victor H. Agreda; Ronnie D. Lilly, both of Kingsport, Tenn.

[73] Assignee: Eastman Kodak Company, Rochester, N.Y.

[21] Appl. No.: 354,578

[22] Filed: May 22, 1989

[51] Int. Cl.$^5$ .................. C07C 67/08; C07C 67/54; B01D 3/40

[52] U.S. Cl. .................................. 560/265; 560/248; 203/35; 203/38; 203/51; 203/61; 203/DIG. 6

[58] Field of Search .............. 203/38, DIG. 6, 35, 203/34, 29, 61, 51; 560/265, 248; 202/158; 422/187

[56] References Cited

U.S. PATENT DOCUMENTS

| | | | |
|---|---|---|---|
| 2,155,625 | 4/1939 | von Retze | 560/265 |
| 3,927,077 | 12/1975 | Finkbeiner et al. | 560/265 |
| 4,304,925 | 12/1981 | Watanabe et al. | 560/248 |
| 4,435,595 | 3/1984 | Agreda et al. | 560/234 |
| 4,497,967 | 2/1985 | Wan | 560/265 |
| 4,526,725 | 7/1985 | Deardorff | 560/265 |
| 4,597,834 | 7/1986 | Berg et al. | 560/248 |

Primary Examiner—Wilbur Bascomb
Attorney, Agent, or Firm—Charles R. Martin; William P. Heath, Jr.

[57] ABSTRACT

In a process for the production of methyl acetate from methanol and glacial acetic acid involving countercurrently flowing acetic acid and methanol through a single reactive distillation column having an extractive distillation section and a methyl acetate/acetic acid rectification section to obtain methyl acetate in the presence of an acidic catalyst, the improvement which comprises producing ultra high purity methyl acetate by the additional step of introducing acetic anhydride and a salt-free acid catalyst into the reactive distillation column between the extractive distillation section and the methyl acetate/acetic acid rectification section.

4 Claims, 1 Drawing Sheet

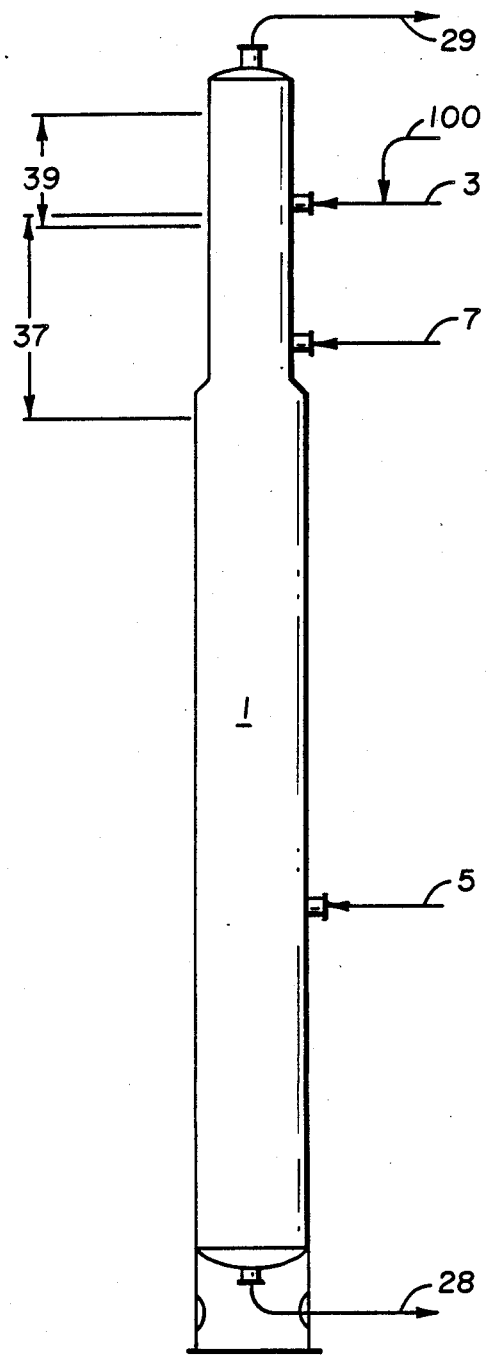
Fig.

PREPARATION OF ULTRA HIGH PURITY METHYL ACETATE

This invention relates to preparation of methyl acetate of ultra high purity by introducing acetic anhydride and a salt-free acid catalyst into a reactive distillation column.

U.S. Pat. No. 4,435,595 discloses a process for the preparation of high purity methyl acetate from methanol and glacial acetic acid. In this process approximately stoichiometric quantities of acetic acid and methanol are counter-currently flowed through a reactive distillation column in the presence of a catalytic amount of an acidic catalyst.

Although the quality of the methyl acetate produced by this process is very good there is a need for even higher purity methyl acetate. Furthermore, when the quality of the methyl acetate produced by this process decreases due to operation at high rates or other reasons, there is a need to increase the purity of methyl acetate.

We have now discovered that the purity of the methyl acetate produced by the process disclosed in U.S. No. 4,435,595 can be improved by introducing acetic anhydride and a salt-free acid catalyst into the reactive distillation column between the extractive distillation section and the methyl acetate/acetic acid rectification section.

By the term "ultra high purity methyl acetate" we mean methyl acetate which is at least 99.5 weight percent methyl acetate, based on the weight of the methyl acetate and impurities.

The following description and the FIGURE are helpful in fully understanding this invention. The reactive distillation column in the FIGURE, as well as the numbered references, correspond identically to the reactive distillation column and numbered references in FIG. 2 of U.S. No. 4,435,595. For simplification, vapor sidedraw, liquid sidedraw, reflux and other features of the distillation column shown in FIG. 2 of U.S. No. 4,435,595 are not shown in the FIGURE but it will be understood that the reactive distillation column in the FIGURE is the same reactive distillation column as that shown in FIG. 2 of U.S. No. 4,435,595 and operates in accordance with the disclosure of U.S. No. 4,435,595, the entirety of which is herein incorporated by reference.

In order to understand the present invention it is first necessary to understand how the reactive distillation column operates. Referring to the FIGURE, glacial acetic acid is fed to distillation column 1 provided through stream 3. Methanol is fed to the column through stream 5. Sulfuric acid catalyst is fed through stream 7 to the lower portion of the extractive distillation section of the column. Heat or live steam is applied to the base of the column by a means not shown. Acetic acid and methanol react within the column to form methyl acetate and water. The column bottoms, containing mostly water and acid catalyst, are removed as stream 28, and the methyl acetate is removed as stream 29.

The extractive distillation section of the column is designated as 37. In this region, which is rich in acetic acid, the primary phenomenon taking place is the breaking of the azeotropes by the extractive action of the acetic acid.

The area designated as 39 is the methyl acetate/acetic acid rectification section of the column. In this section methyl acetate is separated from the acetic acid reactant. The acetic acid descends through the column and the methyl acetate is taken overhead through stream 29.

In accordance with the present invention the reactive distillation column has been modified such that stream 100, composed of acetic anhydride and a salt-free acid catalyst, is introduced into reactive distillation column 1 between the extractive distillation section 37 and the methyl acetate/acetic acid rectification section 39 by introducing stream 100 into stream 3. Since the extractive distillation section and the methyl acetate/acetic acid rectification section overlap somewhat there is no region actually "between" these two sections in the sense one section starts where the other section stops. Therefore by the term "between" we mean that stream 100 is introduced into the column in the general region where these two sections come together.

The acid catalyst that can be used in this invention can broadly be described as an organic or inorganic acid capable of accelerating the rate of the reactions between acetic anhydride and methanol and acetic anhydride and water without itself being consumed in the reactions. Specifically, the catalyst can be sulfuric acid, p-toluenesulfonic acid or phosphoric acid.

The acid catalyst used in this invention is salt-free. By the term "salt-free" we mean that there are no substantial quantities of insoluble mineral salts in the catalyst. The maximum amount of salt that the acid catalyst can contain depends on the types of salts contained in the acid catalyst, the amount of catalyst used, and the temperature at which the column is operated. For example, high purity sulfuric acid containing less than 0.1 parts per million salts is a suitable catalyst for normal feed rates and operating conditions.

The amounts of salt-free acid catalyst in stream 100 can vary widely but preferably the amount of catalyst is in the range of 0.05 to 0.5, lb of catalyst per pound of the combined amount of acitic acid and acetic anhydride fed to the reactive distillation column.

The amount of acetic anhydride in stream 100 can vary widely but preferably the amount of acetic anhydride is in the range of 1 to 10 weight percent of the amount of acetic acid fed to the reactive distillation column.

In the preferred embodiment shown in the FIGURE the acetic anhydride and the salt-free acid catalyst are mixed together and introduced into acetic acid stream 3 and the combined stream is then introduced into the column. Optionally, the acetic anhydride and salt-free acid catalyst can be mixed together and introduced into the column as a separate stream in addition to stream 3. If desired, the acetic anhydride and salt-free acid catalyst can be introduced into the column as individual streams.

An important advantage of this invention is that it provides a means to enhance the purity of the methyl acetate when the purity deteriorates due to the use of wet acetic acid, excessive buildup of intermediate boiling impurities, operation at production rates above design capacity or some other reason.

EXAMPLE 1

The process disclosed in U.S. No. 4,435,595 was operated with the acetic acid feed containing no acetic anhydride and salt-free acid catalyst. The overhead stream contained 98.3 weight percent methyl acetate.

EXAMPLE 2

The process disclosed in U.S. No. 4,435,595 was operated with the acetic acid feed containing 2.8 weight percent acetic anhydride but no salt-free acid catalyst. The overhead stream contained 98.3 weight percent methyl acetate.

EXAMPLE 3

The process disclosed in U.S. No. 4,435,595 was operated with the acetic acid feed containing 4.1 weight percent acetic anhydride and 0.48 lbs. salt-free sulfuric acid per 100 lbs. of acetic acid plus acetic anhydride. The overhead stream contained 99.7 weight percent methyl acetate.

Examples 1 and 2 illustrate that when the invention is not practiced the purity of methyl acetate is only 98.3 percent but when the invention is practiced as illustrated in Example 3 the purity of the methyl acetate is increased to 99.7 percent.

We claim:

1. In a process for the production of methyl acetate from methanol and glacial acetic acid wherein the acetic acid functions both as reactant and as extractive agent, the process comprising the steps of
   (a) selecting a design for a single reactive distillation column which provides intimate contact sufficient to enable acetic acid to be used both as a reactant and as an extractive agent within the column, the column having an extractive distillation section and a methyl acetate/acetic acid rectification section located above the extractive distillation section,
   (b) selecting a residence time for the single reactive distillation column which provides intimate contact sufficient to enable acetic acid to be used both as a reactant and as an extractive agent within the column,
   (c) countercurrently flowing approximately stoichiometric quantities of said acetic acid and methanol through the single reactive distillation column in the presence of a catalytic amount of an acidic catalyst so as to provide intimate contact in the column between the acetic acid and methanol, between the acetic acid and methyl acetate/water azeotrope, and between the acetic acid and methyl acetate/methanol azeotrope, the residence time in the column being sufficient to accomplish high reactant conversion and to obtain methyl acetate, and
   (d) continuously removing methyl acetate from the top of the single column and continuously removing water from the bottom of the column, the improvement which comprises producing ultra high purity methyl acetate by the additional step of introducing acetic anhydride and a salt-free acid catalyst into the single reactive distillation column between the extractive distillation section and the methyl acetate/acetic acid rectification section.

2. The process of claim 1 wherein the salt-free acid catalyst is selected from the group consisting of sulfuric acid, p-toluenesulfonic acid or phosphoric acid.

3. The process of claim 1 wherein the amount of the salt-free acid catalyst is in the range of 0.05 to 0.5 lb of catalyst per pound of the combined amount of acetic acid and acetic anhydride fed to the reactive distillation column.

4. The process of claim 1 wherein the amount of acetic anhydride in the range of 1 to 10 weight percent of the amount of acetic acid fed to the reactive distillation column.

* * * * *